United States Patent [19]

Elmaleh et al.

[11] Patent Number: 4,617,386

[45] Date of Patent: Oct. 14, 1986

[54] PROCESS FOR THE PRODUCTION OF $^{18}$F-2-DEOXY-2-FLUORO-D-GLUCOSE

[75] Inventors: David R. Elmaleh, Brookline, Mass.; Shlomo Levy, Jerusalem, Israel; Chyng-Yann Shiue, East Setauket; Alfred P. Wolf, Setauket, both of N.Y.

[73] Assignee: The United States of America as represented by the United States Department of Energy, Washington, D.C.

[21] Appl. No.: 488,311

[22] Filed: Apr. 25, 1983

[51] Int. Cl.$^4$ .............................................. C07H 1/00
[52] U.S. Cl. .................................. 536/122; 536/18.4; 536/18.5; 536/124
[58] Field of Search .................. 536/1.1, 4.1, 18.1, 536/18.3, 18.4, 118, 120, 122, 18.5, 124

[56] References Cited

U.S. PATENT DOCUMENTS

| | | | |
|---|---|---|---|
| 3,632,804 | 1/1972 | Gray et al. | 536/118 |
| 3,970,643 | 7/1976 | Woo et al. | 336/13.5 |
| 4,156,776 | 5/1979 | Mufti et al. | 536/1.1 |

FOREIGN PATENT DOCUMENTS 0966837 8/1964 United Kingdom ................ 536/4.1

OTHER PUBLICATIONS

Ishido et al., *Chemical Abstracts*, vol. 95, 1981, No. 220273t.
Levy et al., *Chemical Abstracts*, vol. 98, 1983, No. 194270e.
Olesher et al., *Chemical Abstracts*, vol. 98, 1983, No. 198616v.
Levy et al., *Chemical Abstracts*, vol. 98, 1983, No. 34857y.

*Primary Examiner*—Johnnie R Brown
*Assistant Examiner*—Elli Peselev
*Attorney, Agent, or Firm*—Margaret C. Bogosian; James W. Weinberger; Judson R. Hightower

[57] ABSTRACT

Process for the production of 2-deoxy-2-fluoro-D-glucose and the corresponding $^{18}$F-compound in which methyl 4,6-O-benzylidine-3-O-methyl-2-O-trifluoromethanesulfonyl-$\beta$-D-mannopyranoside is reacted with a triflating reagent, the resulting compound reacted with CsHF$_2$, RbF or the corresponding $^{18}$F-compounds, and thereafter the alkyl groups removed by hydrolysis.

5 Claims, No Drawings

PROCESS FOR THE PRODUCTION OF $^{18}$F-2-DEOXY-2-FLUORO-D-GLUCOSE

BACKGROUND OF THE INVENTION

The United States Government has rights in this invention pursuant to Contract No. DE-AC02-76CH00016, between the U.S. Department of Energy and Associated Universities, Inc.

This invention relates to 2-deoxy-2-[$^{18}$F]fluoro-D-glucose ($^{18}$FDG) and to methods of preparing it. More particularly, it relates to novel procedures for the preparation of this known compound. It relates also to novel intermediates useful for the preparation of this valuable compound.

The development of a rapid synthetic procedure to produce $^{18}$FDG using $^{18}$F-labeled elemental fluorine ([$^{18}$F]F$_2$) or [$^{18}$F]CH$_3$COOF coupled with the development of positron emission transaxial tomography (PETT) and appropriate mathematical models has made it possible to measure local cerebral glucose metabolism in man non-invasively. This has generated intense interest in the biomedical community in the use of $^{18}$FDG and PETT to study the correlation of metabolism and function in a variety of human pathologies as well as normal activity.

As a result of this interest, many cyclotron (accelerator)-PETT centers have instituted, or are in the process of instituting, the targetry and synthesis system required for producing this radiotracer. These $^{18}$FDG synthesis systems have been based on minor modifications of the $^{18}$FDG synthesis originally reported by Ido, et al., *J. Org. Chem.* 42: 2341 (1977) and *J. Label. Cmpds. Radiopharm*, 14: 175 (1978). A major problem in meeting increasing demands for this tracer is that many cyclotron-PETT centers have medical cyclotrons which do not have the optimal deuteron energies for $^{18}$F production via the $^{20}$Ne(d,α)$^{18}$F reaction described by Casella, et al., *J. Nucl. Med.*, 21: 750 (1980). This, together with the low chemical yield from the original $^{18}$FDG synthesis (about 10%), imposes a limitation on the capabilities of many centers to synthesize sufficient $^{18}$FDG for their own needs. This interferes with the ability of many centers, which cannot synthesize their own $^{18}$FDG, to use this tracer since if they are to obtain the tracer from an outside source, the centers where it can be produced must be located within a 2 to 3 hour shipping radius from the institution using the tracer. It is apparent then, that the development of an improved synthesis of $^{18}$FDG would make it possible for institutions with small medical cyclotrons or other accelerators to produce sufficient quantities of $^{18}$FDG for their own daily use and would allow the production of multiple dose batches of $^{18}$FDG by institutions with cyclotrons of higher production capacity.

DETAILED DESCRIPTION OF THE INVENTION

A procedure has now been discovered for the preparation of $^{18}$FDG which permits the rapid, facile production of this compound in highly purified form at a yield which is much higher than the yield which can be achieved with conventional methods.

In accordance with the practice of this invention, $^{18}$FDG is produced by the sequence of reactions shown in Reaction Scheme 1.

The first step of the reaction sequence is the preparation of the novel methyl 4,6-O-benzylidene-3-O-methyl-2-O-trifluoromethanesulfonyl-β-D-mannopyranoside (Compound 2) with trifluoromethanesulfonic anhydride as a triflating reagent. The reaction can also be effected with the corresponding acid halide, suitably the acid chloride.

The reaction is carried out by reacting methyl 4,6-O-benzylidene-3-O-methyl-β-D-mannopyranoside (Compound 1) with the selected triflating reagent in an inert organic solvent at a low temperature, e.g. 0° to 30° C. in the presence of an alkaline reagent. It is preferred to use an inert atmosphere such as nitrogen to limit side reactions.

With the preferred anhydride, i.e. triflic anhydride, the reaction is carried out in an inert organic solvent, suitably in ether, hydrocarbon or halogenated hydrocarbon containing up to eight carbon atoms at a temperature of from about 20° to 30° C. for a period of from 1 to 2 hours. Suitable solvents include methylene chloride, ethylene dichloride or ethyl ether. The anhydride is preferred since the reaction is easier to control than with the acid halide and takes place at about room temperature.

Reaction Scheme 1

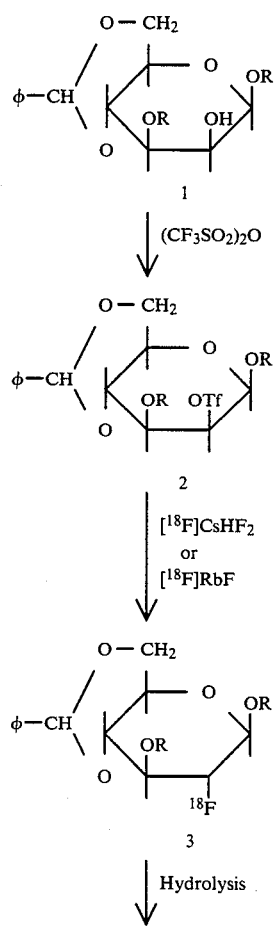

-continued
Reaction Scheme 1

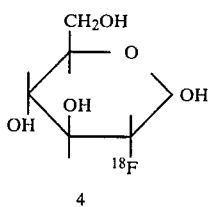

4

It is preferred to use a slight molar excess of the trifluoromethanesulfonic anhydride, for example up to about 3% molar excess.

The preferred alkaline reagents are nitrogenous organic bases which are soluble in the solvent, for example pyridine. The alkaline reagent is designed to neutralize the acid by-product of the principal reaction. Therefore, the amount employed will be at least the molar equivalent of the expected acid. Typically a slight excess, e.g. up to 10%, will be employed.

The products can be isolated by any convenient procedure. One such procedure is illustrated in the examples.

The next step is the conversion of Compound 2 to methyl 4,6-O-benzylidene-2-[$^{18}$F]fluoro-2-deoxy-3-O-methyl-$\beta$-D-glucopyranside (Compound 3) by reaction with a fluorinating agent which is [$^{18}$F]RbF or [$^{18}$F]CsHF$_2$.

Reaction is effected in an inert, anhydrous organic solvent at a temperature of from about 100° C. to 150° C., preferably 120° C. to 140° C. The reaction time is typically 10 to 30 minutes, with higher temperatures favoring shorter reaction periods. In the preferred temperature range, the reaction period is 20 to 30 minutes. Typically useful solvents include dimethylformamide (DMF) and hexamethylphosphoric triamide (HMPA).

The reaction is, of course, applicable to the preparation of $^{18}$F compounds and $^{19}$F compounds. In the latter case, a molar excess of the fluorinating compound will be employed, e.g. up to about 10% molar excess. In the former case, there is not a pressing necessity to obtain an extremely high yield since the product is used very soon after its preparation while it is still radioactive. The fluorinating agent, therefore, is not necessarily used in molar excess. In fact, since the fluorinating agent is the more expensive of the two reactants, it is common to use an excess of the mannopyranoside.

The desired product can be isolated by any of a number of procedures. One especially useful process is illustrated in the examples.

The triflated compounds, which may be produced by the foregoing processes, are novel, and are specifically included within the scope of this invention. They may be represented by the formula:

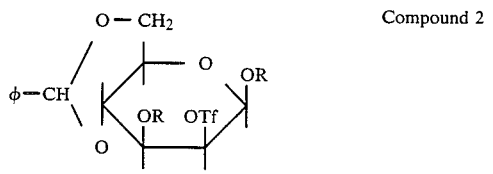

Compound 2 wherein R is methyl, ethyl or propyl and Tf is trifluoromethanesulfonyl. To produce the ethyl or propyl compounds the ethyl or propyl homologs of Compound 1 will be employed.

The compounds [$^{18}$F]CsHF$_2$ and [$^{18}$F]RhF are known compounds which can be prepared by known procedures.

$^{18}$FDG is produced by complete hydrolysis of Compound 3 or its homologs to remove the alkyl groups. The preferred hydrolytic agent is BBr$_3$, but BCl$_3$ and concentrated hydrochloric acid are also useful. Hydrolysis with BBr$_3$ produces the desired product in about 90% yield together with a lesser amount of the 3-O-alkyl compound. BCl$_3$ and concentrated HCl produce the same products, but with lesser yields of the desired homologs of Compound 3.

Hydrolysis with concentrated hydrochloric acid or boron trichloride takes place in an inert organic solvent, for example methylene chloride at a temperature of from about 115° C. to 130° C. for a period of from 30 to 60 minutes.

Hydrolysis with BBr$_3$ takes place under less stringent conditions in the same solvents at about 20° C. to 40° C. for a period of from about 25 to 50 minutes.

The hydrolysis products may be separated by column chromatography. In one specific procedure, the hydrolyzate was cooled, evaporated, dissolved in water, heated for five minutes and neutralized, reconcentrated and taken up in 2 ml of aqueous acetonitrile (0.2 ml H$_2$O in 100 ml CH$_3$CN). The solution was then placed on a column of (0.75×30 cm) containing a dry mixture (1:1) of silica gel and alumina. The column was eluted with 10 ml of water-acetonitrile (0.2:100). The purified product eluted in the following 20 ml of water-acetonitrile (5:95). The eluate was evaporated to dryness, saline added, and the solution sterilized by passing through a 0.22$\mu$ millipore filter. The R$_f$ value for $^{18}$FDG is 0.40. The R$_f$ value for the corresponding 3-O-methyl compound is 0.65.

$^{18}$FDG prepared by the process of this invention was characterized by comparison with an authentic sample.

The process of this invention which utilizes the [$^{18}$F-] ion as the fluorinating agent has several advantages over the currently available syntheses of $^{18}$FDG which utilize [$^{18}$F]F$_2$ or [$^{18}$F]CH$_3$COOF. The [$^{18}$F-] fluoride is easier to produce than either of the other reagents in which the fluoride atoms are covalently bonded. This is especially important for institutions which have no cyclotrons with energies higher than 6 MeV deuterons. [$^{18}$F-] can also be generated from a reactor. Additionally with the covalently bonded fluorine compounds there is an inherent loss of 50% of the fluorine activity. This loss does not apply to [$^{18}$F-] compounds.

The following non-limiting examples are given by way of illustration only.

EXAMPLE 1

Preparation of Methyl 4,6-O-Benzylidene-3-O-Methyl-2-O-trifluoromethanesulfonyl-$\beta$-D-Mannopyranoside (Compound 2)

Methyl 4,6-O-benzylidene-3-O-methyl-$\beta$-D-mannopyranoside (324 mg, 1.09 m mole) was dissolved in 10 ml of methylene chloride and 0.5 ml of pyridine, and the solution was cooled to −15° C. under nitrogen. Triflic anhydride (0.19 ml, 1.15 m mole) in 2 ml of methylene chloride was slowly added. The mixture was reacted for 90 minutes at room temperature and washed with cold 10% aqueous sodium bicarbonate. The organic layer was dried and the solvent evaporated under vacuum. The solid was crystallized from 60% ether in hexane to give the desired product in 89% yield, m.p. 113°. Analysis for $C_{16}H_{19}SF_3O_8$

|  | CALCULATED | FOUND |
|---|---|---|
| Carbon | 44.86 | 45.01 |
| Hydrogen | 4.25 | 4.42 |
| Sulfur | 7.47 | 7.43 |

The corresponding ethyl and propyl compounds are similarly prepared.

EXAMPLE 2

Preparation of Methyl 4,6-O-Benzylidene-2-[$^{18}$F]Fluoro-2-Deoxy-3-O-Methyl-$\beta$-D-Glucopyranoside (Compound 3)

Compound 2 (26 mg) and [$^{18}$F]CsHF$_2$ were taken up in 1 ml of freshly distilled DMF in a reaction vial immersed in an oil bath at 130° C. for 25 minutes. The solvent was evaporated and ether and water added. The ether solution was separated, washed twice with water and dried over anhydrous sodium sulfate, and evaporated under a stream of nitrogen to provide the desired compound in over 30% yield.

In another reaction Compound 2 was reacted with [$^{18}$F]CsHF$_2$ (7.2 m Ci) at 130° C. for 25 minutes in freshly distilled (molecular sieve) HMPA. The mixture was extracted with ether, washed with water, the ether layer separated and dried over anhydrous sodium sulfate, and evaporated to give the desired compound (1.5 m Ci, 30% of the activity).

The corresponding ethyl and propyl compounds are similarly prepared.

EXAMPLE 3

Hydrolysis Reactions to Produce $^{18}$FDG (A) With Boron Trichloride: A small amount of the product of Example 2 was taken up in 5 ml of a one molar solution of BCl$_3$ in methylene chloride and heated for 45 minutes at 130° C. The resulting mixture was separated chromatographically as described above to provide $^{18}$FDG as the principal product together with appreciable amounts of 3-O-methyl-$^{18}$FDG.

(B) With Concentrated Hydrochloric Acid: One ml of concentrated HCl was added to an ether extract of Example 2 in a tube and the tube sealed. The mixture was held at 125° C. for 45 minutes and separated chromatographically as described above. The yield was 40% of $^{18}$FDG and 60% of 3-O-methyl-$^{18}$FDG.

(C) With Boron Tribromide: A small amount of the product of Example 2 was taken up in 3 ml of one molar BBr$_3$ in methylene chloride and allowed to stand for 30 minutes at room temperature. The resulting mixture was separated chromatographically as described above. The yield was 90% $^{18}$FDG and 10% 3-O-methyl-$^{18}$FDG.

We claim:

1. A process for the production of $^{18}$F-2-deoxy-2-fluoro-D-glucose which comprises the steps of:
    (a) producing a compound of the formula:

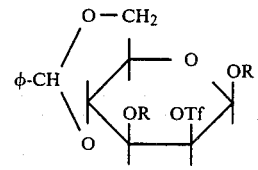

where R is methyl, ethyl or propyl and Tf is trifluoromethanesulfonyl by reaction of the corresponding methyl, ethyl or propyl compounds with trifluoromethanesulfonyl anhydride at 0° C. to 30° C. in an inert organic solvent in the presence of a nitrogenous organic base which is soluble in the solvent;
    (b) reacting the resulting compound with a fluorinating agent which is [$^{18}$F]CsHF$_2$ or [$^{18}$F]RbF in an inert organic solvent with heating at 100° C. to 150° C.; and
    (c) hydrolyzing the resulting compounds to remove the alkyl groups with BBr$_3$, BCl$_3$ or concentrated hydrochloric acid.

2. The process of claim 1, wherein the reaction described in step a is conducted at a temperature in the range of from about 20° C. to 30° C. for a period of from 1 to 2 hours.

3. The process of claim 1, wherein the reaction described in step b is conducted at a temperature in the range of from about 120° C. to 140° C. for a period of from 10 to 30 minutes.

4. The process of claim 1, wherein the reaction described in step c is conducted at a temperature in the range of from about 20° C. to 40° C. for a period of from 25 to 50 minutes.

5. A process as in claim 1, wherein R is methyl.

* * * * *